United States Patent
Vilenskii et al.

(10) Patent No.: US 10,635,797 B2
(45) Date of Patent: Apr. 28, 2020

(54) METHOD AND ELECTRONIC DEVICE FOR DETERMINING WHETHER TO ALLOW USER ACCESS

(71) Applicant: Samsung Electronics Co., Ltd, Suwon-si, Gyeonggi-do (KR)

(72) Inventors: Maksim Alexeevich Vilenskii, Moscow (RU); Andrey Vladimirovich Kletsov, Moscow (RU); Aleksei Andreevich Gavron, Moscow (RU); Alexander Gennadyevich Chernokalov, Moscow (RU)

(73) Assignee: Samsung Electronics Co., Ltd., Suwon-si (KR)

( * ) Notice: Subject to any disclaimer, the term of this patent is extended or adjusted under 35 U.S.C. 154(b) by 179 days.

(21) Appl. No.: 15/851,612

(22) Filed: Dec. 21, 2017

(65) Prior Publication Data

US 2018/0181734 A1 Jun. 28, 2018

(30) Foreign Application Priority Data

Dec. 26, 2016 (RU) ................................ 2016151280

(51) Int. Cl.
*G06F 21/00* (2013.01)
*G06F 21/32* (2013.01)
(Continued)

(52) U.S. Cl.
CPC ............ *G06F 21/32* (2013.01); *A61B 5/0531* (2013.01); *A61B 5/1172* (2013.01); *G06F 3/044* (2013.01);
(Continued)

(58) Field of Classification Search
CPC .......... G06F 21/30; G06F 21/31; G06F 21/32; G06F 21/50; G06F 21/316; G06F 21/45;
(Continued)

(56) References Cited

U.S. PATENT DOCUMENTS

| 5,953,441 A | 9/1999 | Setlak |
| 5,990,804 A | 11/1999 | Koyama |

(Continued)

FOREIGN PATENT DOCUMENTS

| WO | 00/26848 A1 | 5/2000 |
| WO | 01/94902 A2 | 12/2001 |

(Continued)

OTHER PUBLICATIONS

International Search Report dated Mar. 12, 2018 in connection with International Patent Application No. PCT/KR2017/014647.
(Continued)

*Primary Examiner* — Edward Zee

(57) ABSTRACT

The disclosure relates to a method for determining whether to allow user access at an electronic device comprising: detecting a touch by an object on a touch-sensitive area of the electronic device, in which a plurality of electrode pairs are mounted, the plurality of electrode pairs including a first set of electrode pairs and a second set of electrode pairs; determining a subset of the first set of electrode pairs that are in contact with a part of the object; receiving electrical signals from each pair of the determined subset; calculating impedance values of respective parts of the object on the basis of the received electrical signals; determining a ratio of the calculated impedance values for each pair of electrode pairs disposed on mutually perpendicular lines from said the determined subset, and, when a first impedance value for one electrode pair included in electrode pairs disposed on the mutually perpendicular lines is greater than a second impedance value for the other electrode pair in the electrode pairs, the ratio of the calculated impedance values is a ratio of the first impedance to the second impedance; selecting two pairs of electrode pairs disposed on the mutually perpendicular lines with the maximum ratio of the calculated impedance values; and when the maximum ratio exceeds a
(Continued)

predetermined threshold, identifying the object as a living tissue object, and allow access on the electronic device.

18 Claims, 9 Drawing Sheets

(51) Int. Cl.
*A61B 5/1172* (2016.01)
*G06K 9/00* (2006.01)
*G06F 3/044* (2006.01)
*G06F 3/041* (2006.01)
*A61B 5/053* (2006.01)
*G06F 21/31* (2013.01)
*G06F 21/45* (2013.01)
*A61B 5/00* (2006.01)

(52) U.S. Cl.
CPC ............ *G06F 3/0416* (2013.01); *G06F 21/31* (2013.01); *G06F 21/45* (2013.01); *G06K 9/0002* (2013.01); *G06K 9/0012* (2013.01); *A61B 5/6897* (2013.01)

(58) Field of Classification Search
CPC . G06F 21/82; G06F 21/83; H04L 9/32; H04L 9/3226; H04L 9/3231; G06K 9/00107; G06K 9/0012; G06K 9/00006
See application file for complete search history.

(56) References Cited

U.S. PATENT DOCUMENTS

| | | |
|---|---|---|
| 6,181,808 B1 | 1/2001 | Fukuzumi |
| 2007/0014443 A1 | 1/2007 | Russo |
| 2010/0113952 A1 | 5/2010 | Raguin et al. |
| 2014/0270416 A1 | 9/2014 | Minteer et al. |
| 2016/0154988 A1 | 6/2016 | Benkley, III |
| 2017/0124374 A1* | 5/2017 | Rowe ................ G06K 9/00087 |

FOREIGN PATENT DOCUMENTS

| | | |
|---|---|---|
| WO | 2010/051041 A1 | 5/2010 |
| WO | 2015/130809 A1 | 9/2015 |

OTHER PUBLICATIONS

Written Opinion of the International Searching Authority dated Mar. 12, 2018 in connection with International Patent Application No. PCT/KR2017/014647.

Shimamura et al., "Impedance-Sensing Circuit Techniques for Integration of a Fraud Detection Function Into a Capacitive Fingerprint Sensor", IEEE Sensors Journal, vol. 12, No. 5, May 1, 2012, pp. 1393-1401.

Supplementary European Search Report dated Nov. 12, 2019 in connection with European Patent Application No. 17 88 8512, 5 pages.

* cited by examiner

INPUT SIGNAL : 3MHz 100mV
DIFFERENTIAL VOLTAGE MEASURED AT C1

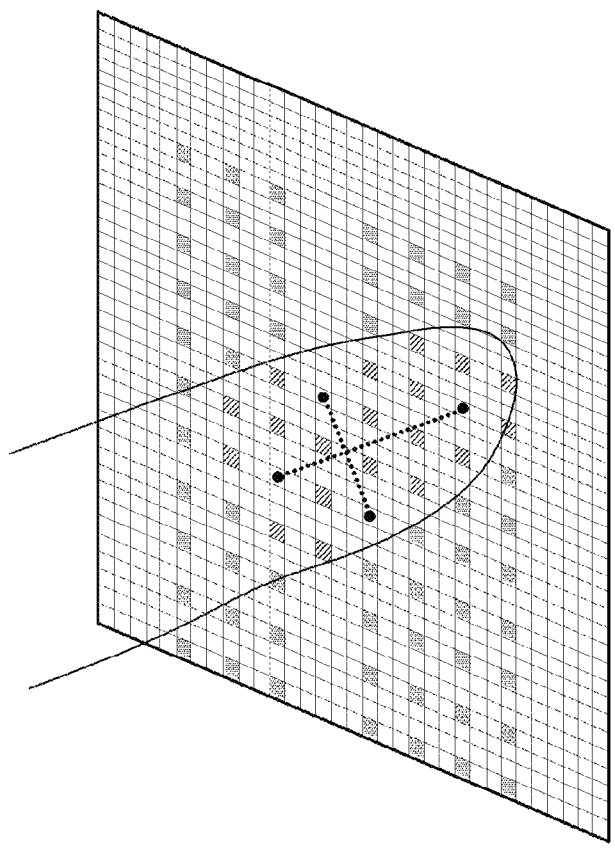
FIG.8
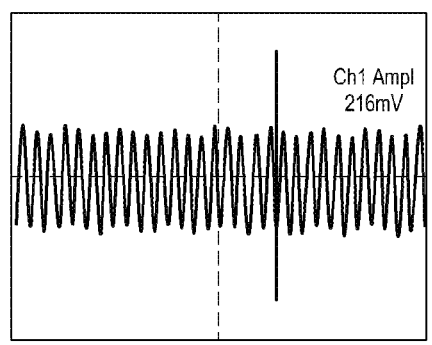 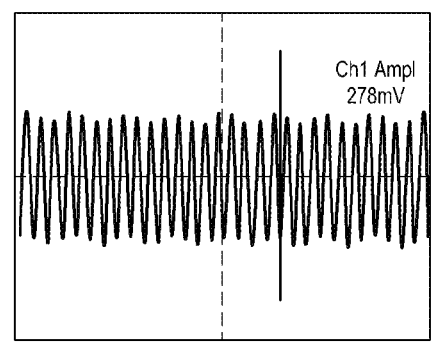
FIG.9A  FIG.9B

METHOD AND ELECTRONIC DEVICE FOR DETERMINING WHETHER TO ALLOW USER ACCESS

CROSS-REFERENCE TO RELATED APPLICATION

The present application is related to and claims priority to Russian Patent Application RU 2016151280 filed Dec. 26, 2016, the disclosure of which is incorporated herein by reference in its entirety.

TECHNICAL FIELD

The present disclosure relates to a method determining whether to allow user access on an electronic device based on recognition of living tissue, and the electronic device performing the method.

BACKGROUND

At present, personal authentication using biometric techniques is one of the most promising and rapidly developing trends, and methods and means that use fingerprints rank highly among such biometric techniques. Existing electronic devices, for example, mobile devices, use capacitive sensors for fingerprint recognition, but the methods employing the sensors may not provide an adequate level of security. Therefore, the existing methods are not ideal to protect devices against unauthorized access. Many studies have shown that such devices can be accessed using fake fingerprints made from play dough, gelatin, silicone, glue, etc. This approach does not provide for anti-spoofing analysis, i.e. a fake detection analysis.

Even if biometric devices use physiologic information to identify the user, conventional methods using capacitive sensors may not detect whether the user applies a "live" finger, i.e., detection of living tissue. Therefore, a user authentication system with a preliminary anti-spoofing analysis is desirable. Thus, a further layer of authentication can be performed by determining whether the user's biometric data is acquired from a real "live" finger.

Certain embodiments as disclosed herein enhance the security of access to devices with biometric authentication when a user having access rights to the device uses an apparatus for registration and appropriate check. According to some embodiments provided by the present disclosure, the anti-spoofing analysis is the result of detecting anisotropy of the tissue in the fingertip.

A conventional biometric authentication system using a fingerprint is disclosed, for example, in patent document U.S. Pat. No. 6,181,808 B1 ("Living Body Discriminating Apparatus", NEC CORPORATION). The disclosure teaches a discriminating apparatus, which is capable to discriminate whether a live finger or a fake was used to input information. The discrimination comprises measuring the potential difference between two muscle points of the finger using at least two electrodes and a grounding electrode, wherein at least two electrodes are disposed in the region of the finger bone. Using a plurality of electrodes and the grounding electrode, a table of potentials can be produced for use in detection of a fake. By analyzing frequency data and data of potentials received from the electrodes, the apparatus determines whether a live finger was used to enter the data. However, such a system does not provide for detection of anisotropy, so a fake made of a material having the same or similar conductivity properties as living tissue can be used.

Such a fake finger may be produced for example, using methods of copying dielectric properties of tissues by mixing water, salt, agar, and polyethylene powder.

Moreover, the aforementioned systems contemplate stringent requirements on the finger position, such as requiring the first joint of the finger to be positioned on the sensor where the grounding electrode is disposed. Further, the measurement period for the aforementioned systems can be quite long (about 0.5 sec) due to the necessity to receive a signal, on the basis of which a data set is determined, in some time interval.

Patent document U.S. Pat. No. 5,990,804 A ("Animate Body Detector" SONY CORPORATION) discloses a detector used to determine whether an object to be checked (fingertip) is an animate body. The determination is made by measuring capacitance, rate of capacitance variation over a predetermined time, moisture and pressure by electrodes and related sensors. This patent document further describes contactless procedure of measuring the listed characteristics. However, the disclosure does not provide for detection of tissue anisotropy either, so a fake can be made of a material having the same or similar conductivity properties as living tissue. At the same time, due to the fact that measurements of variations in living tissue characteristics cannot be made out in parallel, the determination is quite long due to the necessity to acquire various data over time.

Certain embodiments according to the present disclosure provide systems and methods for recognition of living tissue offering higher accuracy of detecting a fake by performing a measurement of anisotropy.

Certain embodiments according to the present disclosure provide a method for recognition of living tissue offering reduced times for identifying whether a sample comprises living or non-living tissue. According to certain embodiments, the identification may take less than 0.3 sec.

The identification of living or fake tissue is attained by embodiments of a method and apparatus such as described in the independent claims. Additional embodiments of the present disclosure are described in the dependent claims.

SUMMARY

To address the above-discussed deficiencies, it is a primary object to provide a preliminary procedure of individual user's registration using physiological information, particularly, a fingerprint, which allows the recognition whether a "live" finger was used to input the physiological information. Certain embodiments as described herein allow implementing a method of identifying living tissue with a conventional capacitive sensor integrated in consumer mobile devices. Furthermore, the present disclosure is also applicable in stationary devices, if appropriate.

In accordance with a method of the present disclosure there is provided a method for determining whether to allow user access based on a user input at electronic device, the method comprising: detecting a touch by an object on a touch-sensitive area of an electronic device, in which a plurality of electrode pairs are mounted, the plurality of electrode pairs including a first set of electrode pairs and a second set of electrode pairs; determining a subset of the first set of electrode pairs that are in contact with a part of the object; receiving electrical signals from each pair of the determined subset; calculating impedance values of respective parts of the object on the basis of the received electrical signals; determining a ratio of the calculated impedance values for each pair of electrode pairs disposed on mutually perpendicular lines from said the determined subset, and, if a first impedance value for one electrode pair included in electrode pairs disposed on the mutually perpendicular lines is greater than a second impedance value for the other electrode pair in the electrode pairs, the ratio of the calculated impedance values is a ratio of the first impedance to the second impedance; selecting two pairs of electrode pairs disposed on the mutually perpendicular lines with the maximum ratio of the calculated impedance values; and if the maximum ratio exceeds a predetermined threshold, identifying the object as a living tissue object, and allow access on the electronic device.

According to certain embodiments of the present disclosure, there is provided an electronic device for determining whether to allow user access based on a user input, the electronic device comprising: a touch-sensitive area configured to detect a touch by an object, wherein a plurality of electrode pairs disposed in the a touch-sensitive area including a first set of electrode pairs and a second set of electrode pairs, and each electrode pair comprises one emitting electrode and one receiving electrode; a generator configured to apply voltage to emitting electrodes of the second set of electrode pairs, and determine a subset of electrode pairs of the second set of electrode pairs that is in contact with a part of the object, wherein the generator is configured to apply voltage to emitting electrodes of the first set of electrode pairs, which are disposed near the determined subset of electrode pairs of the second set; and a first processing circuit configured to receive electrical signals from receiving electrodes of the first set of electrode pairs, which are in a pair with emitting electrodes of the first set of electrode pairs, and calculate impedance values of respective parts of the object on the basis of the received electrical signals, the first set of electrode pairs being electrically coupled with the first processing circuit, wherein the first processing circuit is further configured to determine a ratio of the calculated impedance values for each pair of electrode pairs disposed on mutually perpendicular lines, and if a first impedance value for one electrode pair included in electrode pairs disposed on the mutually perpendicular lines is greater than a second impedance value for the other electrode pair included in the electrode pairs, the ratio of the calculated impedance values is determined as a ratio of the first impedance value to the second impedance value, and adapted to select two pairs of electrode pairs disposed on mutually perpendicular lines with the maximum ratio of the calculated impedance values, if the maximum ratio exceeds a predetermined threshold, identify the object as a living tissue object, and the first processing circuit is configured to allow access on the electronic device.

Before undertaking the DETAILED DESCRIPTION below, it may be advantageous to set forth definitions of certain words and phrases used throughout this patent document: the terms "include" and "comprise," as well as derivatives thereof, mean, without limitation, "include"; the terms "or," is inclusive, meaning "and/or"; the phrases "associated with" and "associated therewith," as well as derivatives thereof, may mean "to include," "be included within," "interconnect with," "contain," "be contained within," "connect to or with," "couple to or with," "be communicable with," "cooperate with," "interleave," "juxtapose," "be proximate to," "be bound to or with," "have," "have a property of," or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

FIG. 8 illustrates schematically how electrode pairs are selected where a plurality of electrode pairs is available, in accordance with one embodiment of the present disclosure;

FIG. 9a illustrates an example of measuring voltage of output signal from one pair of two electrode pairs disposed on mutually perpendicular lines, in accordance with an embodiment of the present disclosure; and FIG. 9b illustrates an example of measuring voltage of output signal from the other pair of two electrode pairs disposed on mutually perpendicular lines, in accordance with an embodiment of the present disclosure.

DETAILED DESCRIPTION

Figure 1:
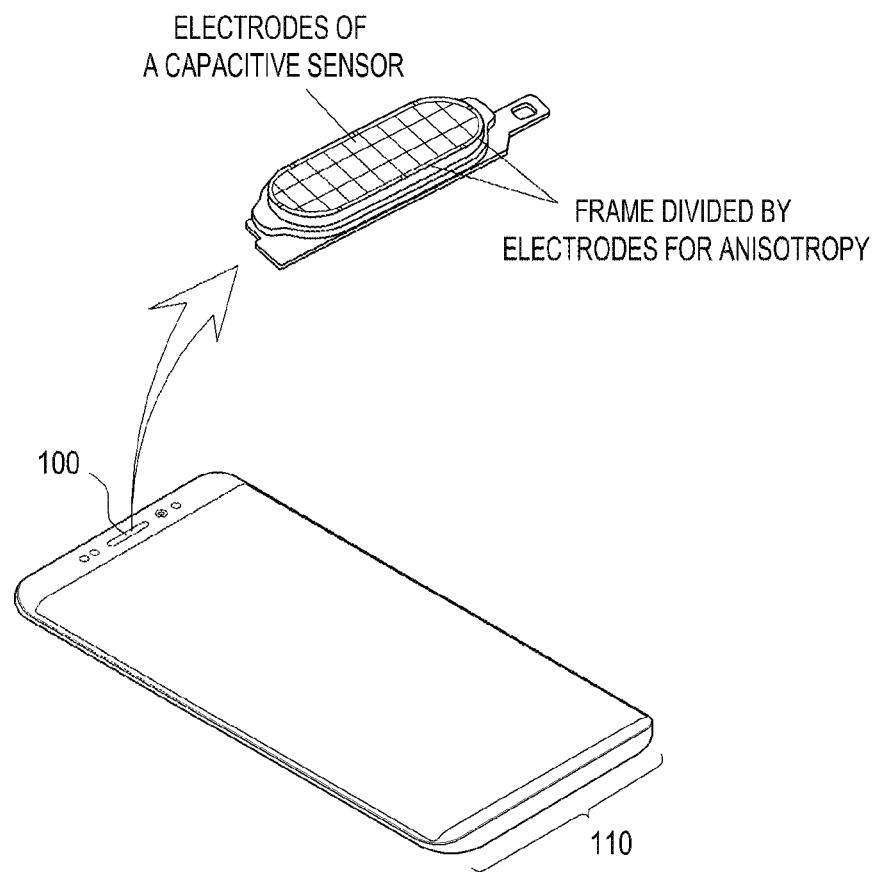
FIG. 1 illustrates an exemplary embodiment of an apparatus for recognition of living tissue in a mobile device in accordance with an exemplary embodiment of the present disclosure.

FIGS. 1 through 9b, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device.

Various embodiments of the present disclosure will be further described in more detail with reference to the drawings. However, the present disclosure may be embodied in many different forms and should not be construed as limited to any specific structure or function presented in the following description. On the basis of the present description those skilled in the art will understand that the scope of the present disclosure encompasses any embodiment of the present disclosure disclosed in this document, regardless of whether it is realized independently or in combination with any other embodiment of the present disclosure. For example, the apparatus may be implemented or the method may be practiced using any number of embodiments described in this document. In addition, it should be understood that any embodiment of the present disclosure disclosed in this document can be implemented using one or more elements of the claims.

The word "exemplary" is used herein to mean "serving as an example or illustration." Any embodiment described herein as "exemplary" should not be necessarily construed as preferred or having an advantage over other embodiments.

As stated above, existing capacitive sensors do not perform anti-spoofing analysis, i.e., detection of living tissue. The present disclosure relates to authentication of a user, comprising a preliminary check for a fake fingerprint, i.e. anti-spoofing analysis. According to some embodiments, this preliminary check for living tissue is performed by measuring anisotropy of the fingertip tissue. Certain embodiments of the present disclosure measure anisotropy of the fingertip tissue, using capacitive sensors modified as will be described below. Existence of anisotropy in the tissue of the fingertip is due to the presence of collagen fibers in the tip of the finger, which make up the bulk of the fingertip and are oriented in a particular direction. Thus, amplitudes of signals measured along and across collagen fibers in the fingertip will substantially vary. Anisotropy can be measured at any point and at any angle of application of a living finger.

According to the present disclosure, anisotropy in the fingertip tissue is measured using electrode pairs disposed on substantially mutually perpendicular lines, such that a device may receive signals measured along and across fibers in the finger. To identify living tissue, certain embodiments of methods according to the present disclosure perform analysis of the ratio of impedance values of all tissues in the fingertip (collagen fibers, capillaries, etc.), in particular, respective regions of tissues, through which an electric signal has passed between electrodes of each of these electrode pairs, and the difference between amplitudes of signals received from each of these electrode pairs, and two electrode pairs are identified, which have maximum ratio and maximum difference between amplitudes of the signals, respectively. Maximum ratio means that orientation of fibers in the tissue coincides with the line on which one electrode pair lies, while the line, on which the second electrode pair lies, is perpendicular to orientation of fibers, hence, the first line as well. Therefore, a pair of electrode pairs disposed on substantially mutually perpendicular lines in the present document means two electrode pairs for which the lines, on which the electrode pairs are disposed, are substantially (approximately) perpendicular, and these two pairs may be disposed relatively close to each other. Therefore, embodiments of a method disclosed in the present disclosure allow detection of "spoofing", i.e. substitution of a real user's finger by an artificial replica repeating the papillary pattern of the user (made e.g. of play dough, clay, gelatin, silicone, glue, etc.) or even a finger belonging to a non-living person.

FIG. 1 illustrates an exemplary arrangement of an apparatus 100 for recognition of living tissue in a mobile device 110 in accordance with a preferred embodiment of the present disclosure.

Referring to FIG. 1, the apparatus 100 for recognition of living tissue can be mounted, for example, under the area of the touch-sensitive "Home" button of the mobile device 110. In some embodiments, the apparatus 100 for recognition of living tissue includes a plurality of electrodes of a capacitive sensor, for detecting anisotropy; each of frames is divided by partial electrodes among the plurality of electrodes.

However, in embodiments the apparatus can be placed under any touch-sensitive area of the screen of the mobile device or, for example, in a frame (generally made of metal) around the aforementioned button.

Figure 2A:
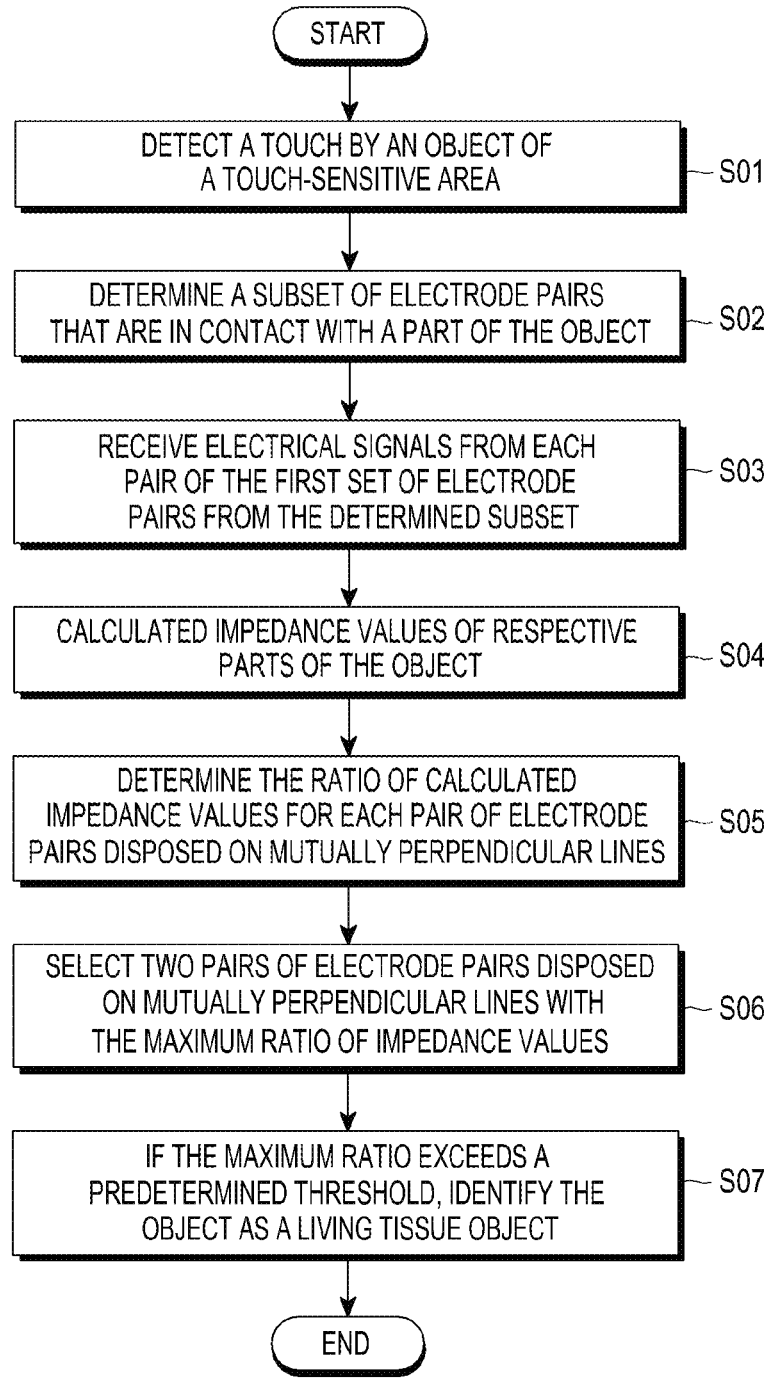
FIG. 2a illustrates a block diagram of the sequence of steps of a method for recognition of living tissue in accordance with an embodiment of the present disclosure.

FIG. 2a illustrates a block diagram of the sequence of steps of a method for recognition of living tissue in accordance with an exemplary embodiment of the present disclosure.

Referring to FIG. 2a, a method for recognition of living tissue may be used in the present disclosure as a preliminary check for granting access to a user's mobile device; however, the scope of the present disclosure is not limited to the aforementioned preliminary check.

In step S01, a touch by an object of a touch-sensitive area on a mobile device is detected, wherein the object is a living tissue object—a fingertip, or a non-living tissue object— such as an artificial replica of a finger or a finger belonging to a non-living person. A plurality of electrodes is mounted under the touch-sensitive area; the electrodes of the plurality are grouped in pairs and form a plurality of fixed electrode pairs.

Figure 2B:
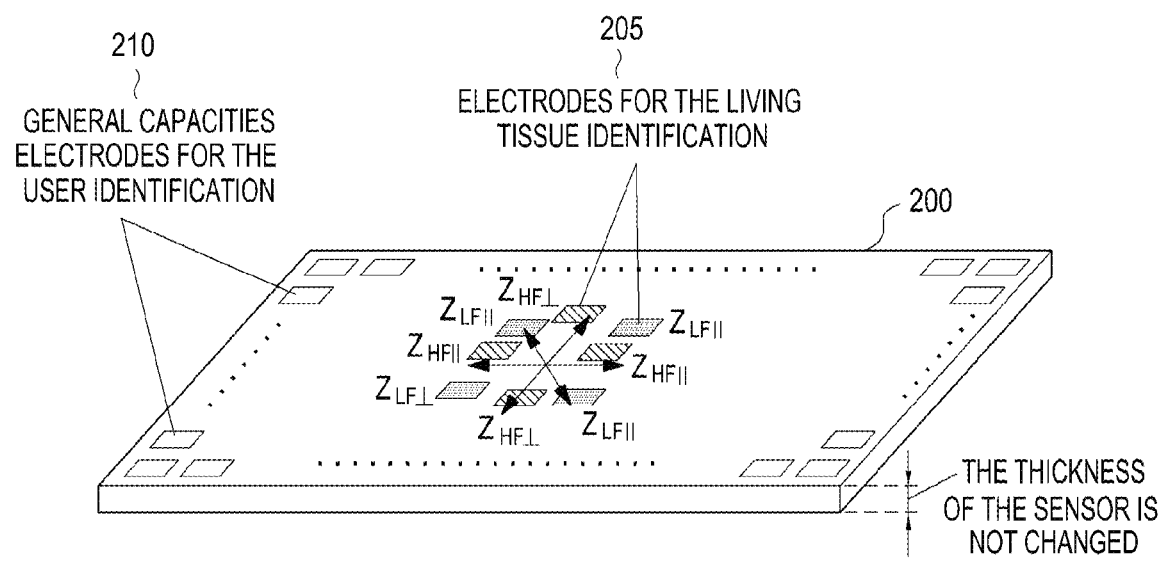
FIG. 2b illustrates a capacitive sensor in accordance with an embodiment of the present disclosure.

According to certain embodiments of the method described in FIG. 2b, the plurality of electrode pairs is included in a capacitive sensor (FIG. 2b, 200), a function of one part (FIG. 2b, 205) of the plurality of electrode pairs in the capacitive sensor (FIG. 2b, 200) is to measure anisotropy, while the remaining electrode pairs (FIG. 2b, 210) are conventional electrodes used in capacitive sensors to measure capacitance. The first part of the plurality of electrode pairs will be further referred to as first set of electrode pairs, and the remaining electrode pairs will be referred to as second set of electrode pairs. Functions of particular fixed electrode pairs may be selected so that both pairs are evenly distributed across the entire surface of the touch-sensitive area, and the lines, on which electrode pairs of the first set are disposed, were directed differently. Electrode pairs of the first set should also be chosen so that lines, on which these pairs are disposed, included line that are pairwise approximately perpendicular to each other. Anisotropy is measured by a subset of electrode pairs of the first set of electrode pairs, which are in contact with the applied object. Two electrode pairs for measurement of anisotropy, disposed on substantially mutually perpendicular lines, are typically in mutual proximity (as close as possible to each other). According to a preferred embodiment, the processes of measuring capacitance for detection of a fingerprint and measuring anisotropy, accomplished by each set of electrode pairs, in the first embodiment are executed in parallel. However, alternate processes are also possible.

Figure 3A:
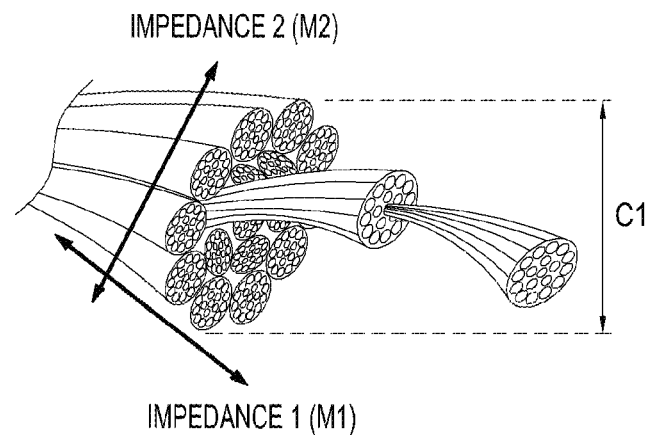
FIG. 3a illustrates a touched area on the touch-sensitive area of the mobile device tissue in accordance with an exemplary embodiment of the present disclosure.
Figure 3A:
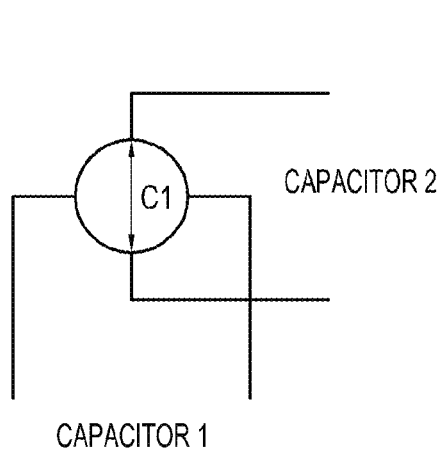
Figure 3A:
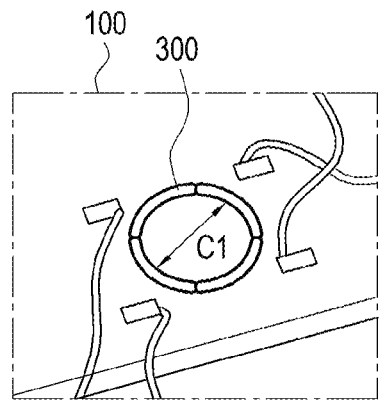

According to another embodiment, the electrode pairs may have dual functionality, i.e., the first set of electrode pairs will coincide with the second set of electrode pairs; in this case, only the subset of those electrode pairs which are in contact with the applied object, is used for measuring anisotropy. Thus, according to this embodiment, all the electrodes function initially as capacitive electrodes. Upon touching by an object the touch-sensitive area on the mobile device, electrical capacitance in the touched area changes, which allows determining the electrodes disposed in this area. FIG. 3a illustrates a touched area on the touch-sensitive area of the mobile device tissue in accordance with an exemplary embodiment of the present disclosure.

Next, electrode pairs in this area are to be selected, which will be used for measuring anisotropy, i.e., electrode pairs, whose current functional characteristics will be modified for measurement of anisotropy. These electrode pairs may be selected according to an algorithm which comprises selecting electrode pairs equally spaced over the touched area such that these pairs were not only in different places of the touched area, but are also differently directed in this area, i.e., the lines, on which the selected electrode pairs are disposed, included at least both parallel or almost parallel lines, and perpendicular or almost perpendicular lines, and intersecting at an angle equal to or close to 45 degrees. In FIG. 3a, for example, the selected electrode pairs are disposed on the perpendicular lines. The remaining (not selected by the algorithm) electrode pairs will still function as capacitive electrodes and be used to measure capacitance for acquisition of image of the fingerprint of the applied object. According to this embodiment, the aforementioned processes performed by a plurality of electrode pairs are preferably executed alternately. However, if appropriate, the electrodes having different purposes at the moment can be also configured for parallel processes. Such use of electrodes not only saves the time spent on recognition, but also saves power due to selection of a restricted subset of electrode pairs by the above algorithm. It should be noted that according to certain embodiments, functional characteristics of the selected electrode pairs can be again changed to measure capacitance in order to acquire the complete image of the fingerprint. As to the first embodiment, the first set of electrode pairs is used only for measurement of anisotropy, therefore, the fingerprint image acquired by the second set of electrode pairs is incomplete, and for checking the match of the papillary pattern, it may be necessary to finish, by interpolating, construction of the image area that was covered with electrode pairs for measurement of anisotropy.

The above subset of electrode pairs that are in contact with the applied part of the object (fingertip) is determined in step S02 both in the case of dual functionality of electrodes, and in the case of two different sets of electrodes, each having own function. In particular, at step S02 a subset of the first set of electrode pairs is identified, which will be used further for measuring anisotropy, as described in greater detail below.

In step S03, electrical signals may be received from each pair of the determined subset of the first set of electrode pairs; input signal is supplied to one electrode of the fixed electrode pair, the emitting electrode, and output signal is read out from the second electrode of the same electrode pair, the fixed electrode pair, and the receiving electrode. Next, in step S04, amplitude of all received electrical signals is measured, and impedance values of respective parts of the applied object are calculated on the basis of the ratio of amplitude of output signals to respective amplitudes of input signals (signal attenuation is proportional to impedance). According to certain exemplary embodiments, such as shown in FIG. 3a, impedance 1 (M1) and impedance 2 (M2) corresponding to input signal (C1) provided to the selected electrode pair are calculated.

In step S05, the ratio of calculated impedance values for each pair of electrode pairs disposed on substantially mutually perpendicular lines from said subset may be determined in order to detect two electrode pairs disposed on substantially mutually perpendicular lines, whose lines extend substantially along and across, respectively, the collagen fibers in the fingertip. It should be noted that according to some embodiments, the ratio of calculated impedance values is the ratio of the greater calculated impedance value to the smaller one if one impedance value for one electrode pair from the pair of electrode pairs disposed on substantially mutually perpendicular lines is greater than the other impedance value of the other electrode pair. In step S06, two pairs of electrode pairs disposed on substantially mutually perpendicular lines with the maximum ratio of impedance values are selected, and if the maximum ratio exceeds a predetermined threshold, the object is identified as a living tissue object at step S07. The threshold may be changed, for example, in the process of entering, by the user, the fingerprint in the phone memory, and chosen, for example, based on the value of the lower impedance (from the pair of compared) or based on the match degree of two impedances (for example, a impedance 1 & impedance 2 in FIG. 3) measured simultaneously by two electrode pairs disposed on substantially perpendicular lines. Significant difference in the impedance values is due to the fact that one signal has passed substantially along the fibers, and the other has passed substantially transversely (see FIG. 3a). Amplitude measured for these signals may also be significantly different.

If the maximum ratio does not exceed a predetermined threshold, the object should be identified as a fake replica of living tissue, because the material, from which this replica is made, is isotropic, or as a finger belonging to a non-living person, which has lost its anisotropic properties. In case of coincidence of harmonic oscillations of signals that passed through the object and were received from two electrode pairs disposed on substantially perpendicular lines, and hence coincidence of amplitudes, a determination is made that the material of the object is isotropic, and, hence, it belongs to a fake finger—an artificial replica or non-living tissue. Therefore, the predetermined threshold may be 1 or substantially close enough to 1 owing to the fact that if impedances are equal their ratio will be 1.

Figure 3B:
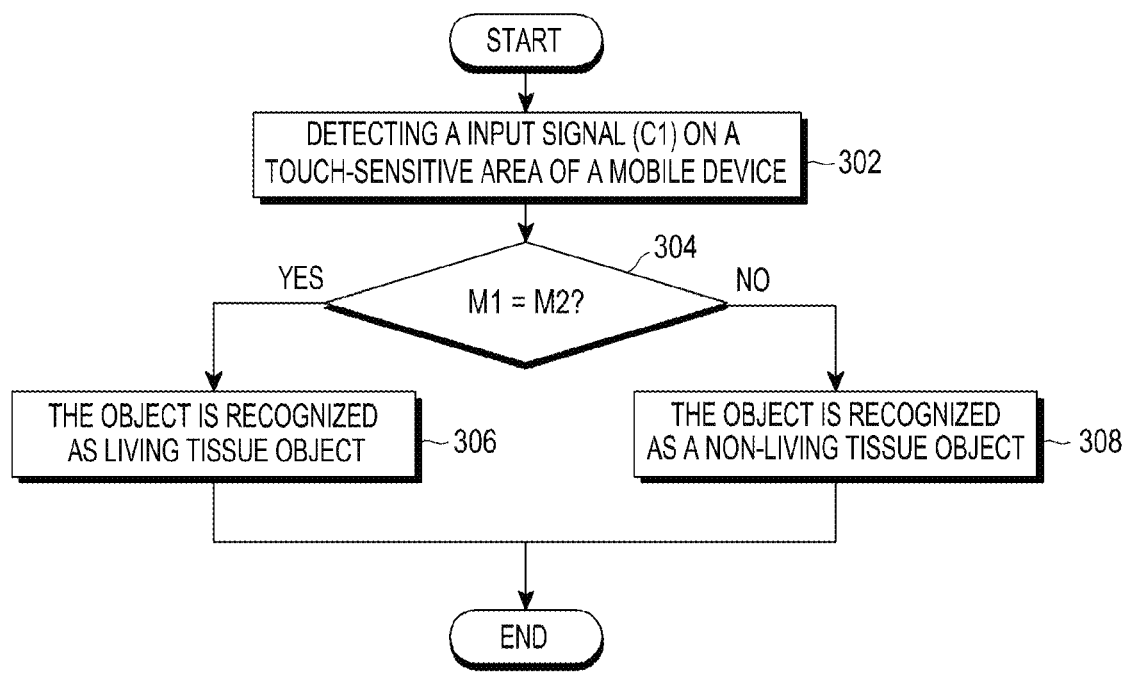
FIG. 3b further illustrates certain processes of operations S06 to S07, such as shown in FIG. 2a in accordance with an exemplary embodiment of the present disclosure.

FIG. 3b illustrates specific processes, such as performed in steps S06 to S07 shown in FIG. 2a, in accordance with an exemplary embodiment of the present disclosure.

Referring to FIG. 3b, in a step 302, on touching by an object, the input signal (C1) is detected on the touch-sensitive area of the mobile device which obtained in S01, and in a step 304, determining whether the impedance 1(M1) and the impedance 2 (M2) calculated for the input signal (C1) are the same, wherein the impedance 1(M1) and the impedance 2 (M2) are the same as those in the embodiment in which the predetermined threshold may be 1. If a result of the determining indicates that the impedance 1(M1) and the impedance 2 (M2) are the same, in a step 306, the object is recognized as living tissue object. If the result of the determining indicates that the impedance 1(M1) and the impedance 2 (M2) are not the same, in a step 308, the object is recognized as a non-living tissue object.

Furthermore, embodiments of methods according to the present disclosure can, for example, deny access to the mobile device if the object is identified as a non-living tissue object. In such cases, the check for match of the papillary pattern may not performed. If parallel processes, such as identification of living tissue and checking for a match of the papillary pattern, are performed using different subsets of electrode pairs, the check process terminates immediately after receiving a negative result of recognition of living tissue.

According to some embodiments, the method further comprises a step in which data relating to the fingerprint is collected using the second set of electrode pairs to identify the user. This step is performed only if the living tissue recognition result is successful, i.e., the object is identified as a living tissue object. In the present disclosure, the object is a fingertip. The collected data respectively includes information relating to the papillary pattern on the fingertip.

If the information relating to the papillary pattern on the fingertip does not match with pre-stored information of the papillary pattern on the fingertip for the user of the mobile device, access to the mobile device is not provided.

According to certain embodiments, including devices having a great number of electrodes, the object can be detected at application to the touch-sensitive area on the mobile device at an arbitrary angle and in any position. The plurality of electrodes forms a grid of electrodes, which covers the entire touch-sensitive area.

Figure 4:
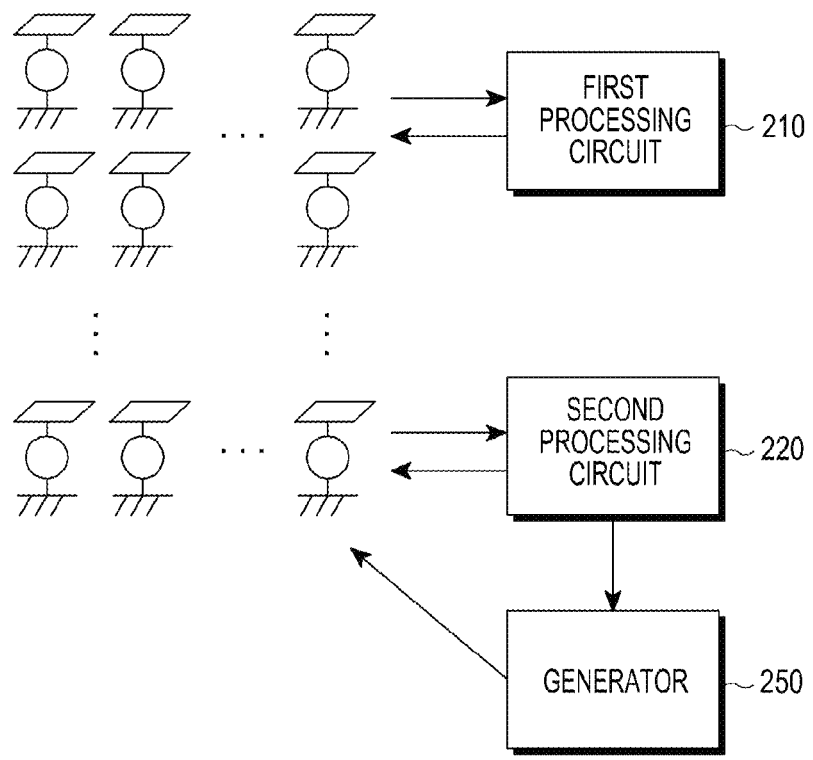
FIG. 4 illustrates an exemplary schematic diagram of an apparatus for recognition of living tissue in accordance with an embodiment of the present disclosure.

FIG. 4 illustrates an exemplary schematic diagram of an apparatus for recognition of living tissue in accordance with certain embodiments of the present disclosure. The apparatus for recognition of living tissue as a preliminary check for granting access comprises a plurality of electrode pairs disposed in a touch-sensitive area on a mobile device. As stated above, the plurality of electrode pairs may include a first set of electrode pairs and a second set of electrode pairs, each having own functionality. One electrode pair includes an emitting electrode, to which a signal is supplied, and a receiving electrode, from which a signal is read out. According to another embodiment, the first set of electrode pairs may coincide with the second set of electrode pairs, i.e., all electrode pairs may be adapted to implement dual functionality.

According to another embodiment, a first set of electrode pairs may be made separately, for example, in a metal frame surrounding a touch-sensitive button. In this case, a second set of electrode pairs forms a grid covering the entire space under the touch-sensitive button.

According to certain embodiments, device for recognition of living tissue further comprises a generator 250 adapted to apply voltage to the plurality of electrode pairs. In particular, the generator 250 may supply electric input signal to one of the electrodes, emitting electrode, of each respective electrode pair. For each single measurement of anisotropy two electrode pairs disposed on substantially mutually perpendicular lines are required. The generator 250 is adapted to apply voltage to two electrode pairs disposed on substantially mutually perpendicular lines from the first set of electrode pairs, and according to a preferred embodiment the generator applies voltage to two electrode pairs disposed on substantially mutually perpendicular lines twice for subsequently averaging the measurements based on the two obtained values. In particular, at the first application of voltage, voltage is first applied to the first pair of the two electrode pairs, and then to the second pair, while at the second application of voltage, it is done on the contrary—first to the second pair, and then to the first.

Capacitive electrode pairs are adapted to detect a touch by an object of a touch-sensitive area, such as a button, and determine a subset of electrode pairs from the second set of electrode pairs that are in contact with the applied object. To determine then the electrode pairs from the first set of electrode pairs, which are also in contact with the applied object, electrode pairs of the first set, which are disposed in close proximity to the determined subset of electrode pairs of the second set, are determined. Electrode pairs from the first set of electrode pairs, which are in contact with the applied object, are determined in order to avoid unnecessary operations with other electrode pairs of the first set of electrode pairs. It saves both power and time consumed for execution of the aforementioned operations.

According to certain embodiments, an apparatus for recognition of living tissue further comprises a first processing circuit 210 and a second processing circuit 220, each operating with own set of electrode pairs. In particular, the first processing circuit 210 receives and processes electrical signals received from electrode pairs of the first set of electrode pairs, and the second processing circuit 220 receives and processes electrical signals received from the second set of electrode pairs. The first set of electrode pairs is electrically coupled with the first processing circuit, and the second set of electrode pairs is electrically coupled with the second processing circuit, respectively. In some embodiments, if there is a plurality of electrode pairs with dual functionality, the electrode pairs are capable of switching to an appropriate processing circuit. According to a second embodiment, functional characteristics of the first processing circuit and second processing circuit can also be embodied in an integral module, for example, a main processing circuit which is configured to receive and process electrical signals from the entire plurality of electrode pairs.

Having received signals, the first processing circuit 210 processes them and calculates the ratio of impedance values on the basis of the received electric signals, and the first processing circuit 210 can be further adapted to determine the ratio of the calculated impedance values for each pair of electrode pairs disposed on substantially mutually perpendicular lines and to select two electrode pairs disposed on substantially mutually perpendicular lines with a maximum ratio of impedance values. The ratio of calculated impedance values is still the ratio of the greater calculated impedance value to the smaller one if one impedance value for one electrode pair from a pair of electrode pairs disposed on substantially mutually perpendicular lines is greater than the other impedance value. As stated above, if the maximum ratio exceeds a predetermined threshold, the applied object is identified as a living tissue object, i.e. a fingertip. It is clear that the ratio of calculated impedance values may be also the ratio of the smaller calculated impedance value to the greater one with further account that two electrode pairs disposed in substantially mutually perpendicular lines should be selected with a minimum, rather than a maximum ratio of impedance values; in this case, the conclusion that the object belongs to objects of living tissue is made if the minimum ratio is less than a predetermined threshold.

Upon receiving electric signals from the second set of electrode pairs, the second processing circuit 220 derives capacitance information contained in these signals and forms an image of the papillary pattern on the fingertip, a fingerprint image. This step is performed only if the object is identified as a fingertip, since if the object is identified as an artificial replica or a finger belonging to a non-living person (the maximum ratio does not exceed a predetermined threshold), access to the mobile device is denied and the process of forming a fingerprint image is not required.

If the object is identified as a fingertip, the second processing circuit 220 can also be adapted to deny access to the mobile device if information relating to the papillary pattern on the fingertip does not match with pre-stored information of the papillary pattern on the fingertip to the user of the mobile device.

The device for recognition of living tissue further comprises a central processing unit (CPU) for additional authentication of a user, such as a standard processor for implementing security tasks.

Figure 5:
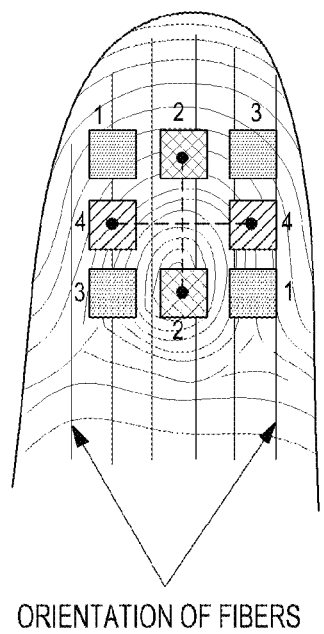
FIG. 5 illustrates schematically how electrode pairs are selected where four electrode pairs are available, in accordance with one embodiment of the present disclosure.

FIG. 5 illustrates schematically how electrode pairs are selected if there are four electrode pairs 1, 2, 3, and 4, according to certain embodiments. The orientation of fibres in the fingertip is depicted approximately in FIG. 3 by vertical lines. If, after measuring voltage of output electrical signals received from each of the electrode pairs 1, 2, 3, and 4, amplitude of signals received from two electrode pairs 1 and 3 disposed on the substantially perpendicular lines is the same or differs slightly, and amplitude of signals received from two electrode pairs 2 and 4 disposed on substantially perpendicular lines is significantly different, it can be concluded that a living tissue, i.e., a live finger is applied. This is due to the fact that the line, on which the electrode pair 2 is disposed, coincides with an orientation of live tissue fibers, and the signal received from this electrode pair 2 was measured along the fibers. The line, on which the electrode pair 4 is disposed, is, on the contrary, perpendicular to the orientation of fibers, and the signal received from the electrode pair 4 was measured across the fibers. If measurement of voltage of output electrical signals received from each of the electrode pairs 1, 2, 3, and 4, shows that amplitude of signals received from the two electrode pairs 1 and 3 disposed on substantially perpendicular lines is the same or differs slightly, and amplitude of signals received from the two electrode pairs 2 and 4 disposed on substantially perpendicular lines is also the same or differs slightly, then the conclusion is made that no living tissue is present, i.e. an artificial replica or a finger belonging to a non-living person was applied.

Figure 6:
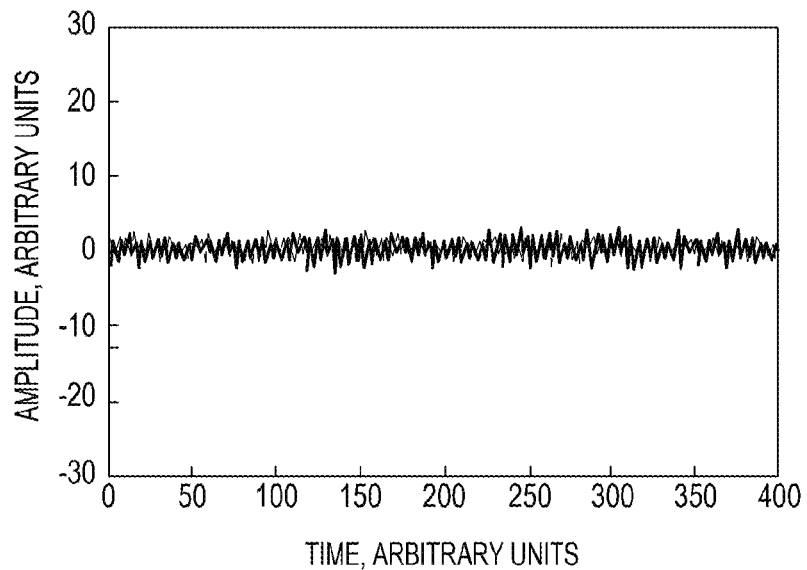
FIG. 6 illustrates a time-based graph of measured amplitudes for signals received from an artificial replica of user's finger.
Figure 7:
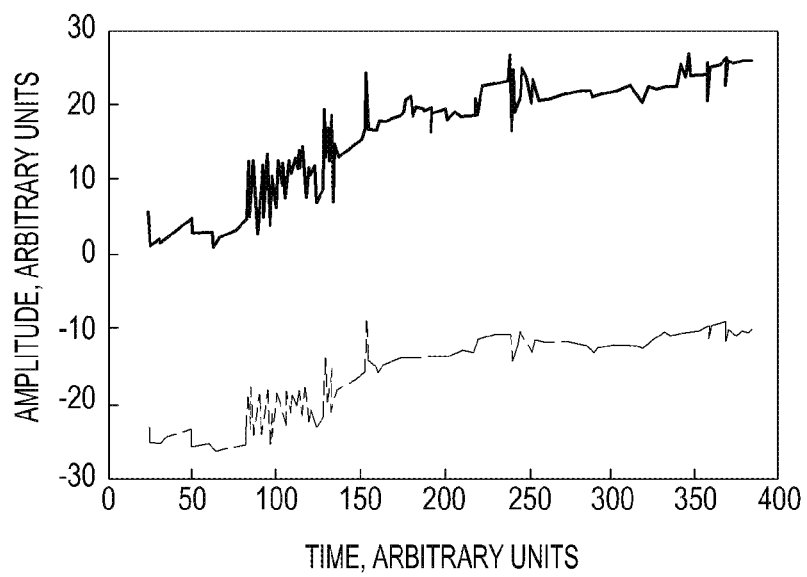
FIG. 7 illustrates a time-based graph of measured amplitudes for signals received from a real living finger of the user.

FIGS. 6 and 7 illustrate time-based graphs of amplitudes of signals received from an artificial replica of the user's finger and a real user's finger, illustrating results of measurements of voltage of output electrical signals described in relation to FIG. 5. FIG. 6 illustrates how in the case of a non-living tissue object, the amplitudes of signals received from two electrode pairs disposed on substantially perpendicular lines are almost identical. In the case of a real finger (see FIG. 7) the time-based graph of amplitudes for one signal is significantly different from the time-based graph of amplitudes for the other signal received from the electrode pair disposed on substantially perpendicular line relative to the line, on which the electrode pair that generated the first signal is disposed.

FIG. 8 illustrates schematically how electrode pairs are selected if there is a plurality of electrode pairs, in accordance with one embodiment of the present disclosure. In particular, this Figure shows a grid of electrodes to be touched by a user's finger. The electrodes depicted in white are conventional electrodes for a capacitive sensor, adapted to measure capacitance for reading out the papillary pattern on the finger, and detecting a user's finger touch. The darkest and grey color against the finger shows electrodes, whose function is to measure anisotropy. Electrodes shown in grey against the finger are the electrodes which are in contact with the applied user's fingertip, as determined by identifying their proximity to the capacitive electrode pairs, which detected the touch. Electrodes for anisotropy measurement, shown in the darkest color, are not in contact with the user's fingertip and, therefore, not actually used in the anisotropy measurement—no electric signal will be supplied to this plurality of electrodes. Electrical signal is supplied to the plurality of electrode pairs shown in grey, and voltage is measured on the basis of this signal over a predetermined time. Output signals are analyzed; amplitude of signals in respect of two electrode pairs disposed on substantially mutually perpendicular lines is compared, and impedances are calculated and compared. Two electrode pairs disposed on substantially mutually perpendicular lines, the output signal of which has a maximum ratio of impedances, are highlighted in the Figure by black circles connected by lines on which the electrode pairs are disposed. Signal received from precisely these two electrode pairs is used to determine whether a real live finger or an artificial replica was applied to the grid of electrodes, in accordance with the method described above.

FIGS. 9a and 9b show an example of measuring voltage of output signals from a pair of electrode pairs disposed on substantially mutually perpendicular lines, in accordance with the embodiment of the present disclosure. The embodiment was illustrated by supplying input electrical signal having frequency of 3 MHz and voltage of 100 mV to a plurality of electrode pairs from the first set of electrode pairs that are in contact with the applied object; a user's finger was applied to the circuit with a plurality of electrode pairs. Therefore, voltage was applied to each emitting electrode from the electrode pair for measuring anisotropy, which is in contact with the applied finger. Output electric signal was read at output of the plurality of electrode pairs (i.e. from each receiving electrode of the aforementioned electrode pair). In particular, frequency and voltage of the output signal can be measured by an oscilloscope, a device for studying amplitude and time parameters of electrical signal, which shows a time-varying voltage waveform.

FIGS. 9a and 9b illustrate two oscillograms depicting harmonic oscillations of voltage of signals that passed through the applied finger and were received from the first electrode pair and the second electrode pair having a maximum difference of the signal amplitude. The oscillogram shown in FIG. 9a illustrates a signal received from the first electrode pair, and the oscillogram shown in FIG. 9b illustrates a signal received from the second electrode pair. The measurement was taken for approximately 10 µs (time scale of the oscillograms is 1 µs per box); however, a greater or lesser time interval may also be used. As seen in the exemplary oscillogram of FIG. 9a, the average amplitude of harmonic oscillations of voltage of this output signal is 216 mV. At the same time, the average amplitude of harmonic oscillations of voltage of the output signal from the second electrode pair (see FIG. 9b) is shown as 278 mV. From here it follows that the line of the first electrode pair coincides with orientation of fibers and the signal received from this electrode pair was measured along the fibers, and the line of the second electrode pair is perpendicular to orientation of fibers and the signal received from this electrode pair was measured across the fibers. Therefore, amplitude of the output signal received from the second electrode pair is greater that amplitude of the output signal received from the first electrode pair, approximately by 1.287 times, which exceeds a predetermined threshold, which can be chosen as $1+\delta$, where $\delta=0.092$, the ratio of variation of amplitudes of sine wave to the average amplitude of the signal. The difference between values of voltage amplitude, equal to 62, also significantly exceeds a second threshold, which may be equal, for example, to 0 or another small value. From the obtained ratio of voltages it can be concluded that the applied finger belongs to a living tissue object. If an artificial replica is applied to a circuit with a plurality of electrode pairs, harmonic oscillations of voltage of signals that passed through the applied artificial replica and were received from the first electrode pair and the second electrode pair will coincide fully or essentially. This example considered, for clarity, the ratio of voltages demonstrating the presence of anisotropy. However, to determine anisotropy in automatic mode it is necessary to measure particularly impedances, because they take into account many different factors, including phase delays. In particular, for computing the anisotropy of impedance the following factors should be also taken into account: resistance of oscilloscope probes; voltage and current offset (to determine complex impedance value). Those skilled in the art should understand that a plurality of electrodes in accordance with embodiments of the present disclosure can be mounted in any touch-sensitive area, depending on the specific practical application, and can be divided into sets having different functionality, or dual function electrodes can be used. The above embodiments were described only as examples, and various modifications of them can be implemented.

Embodiments of the present disclosure may find application in consumer electronic devices and may expand capabilities of electronic devices by ensuring an additional security owing to the present method for recognition of living tissue, which allows identifying an artificial replica of a finger.

Embodiments of the present disclosure may be utilized for performing:

preliminary checks for granting access to electronic devices;

preliminary checks for granting access to personal information; and preliminary checks for granting access to financial transactions, etc.

Those skilled in the art should understand that the number of structural elements or components of the apparatus 100 may vary, if appropriate. In addition, it should be clear that the illustrated arrangement of units of the apparatus 100 is exemplary and can be modified, as necessary, to achieve greater effectiveness in a particular application, if the description does not specifically defines otherwise. References to system elements in the singular do not exclude a plurality of such elements, if not explicitly stated otherwise.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A method for determining whether to allow user access based on a user input at an electronic device, the method comprising:

detecting a touch by an object on a touch-sensitive area of the electronic device, in which a plurality of electrode pairs are mounted, the plurality of electrode pairs including a first set of electrode pairs and a second set of electrode pairs;

determining a subset of the first set of electrode pairs that are in contact with a part of the object;

receiving electrical signals from each pair of the determined subset;

calculating impedance values of respective parts of the object based on the received electrical signals;

determining a ratio of the calculated impedance values for each pair of electrode pairs disposed on mutually perpendicular lines from the determined subset, and, when a first impedance value for one electrode pair included in electrode pairs disposed on mutually perpendicular lines is greater than a second impedance value for the other electrode pair in the electrode pairs, the ratio of the calculated impedance values is a ratio of the first impedance value to the second impedance value;

selecting two pairs of electrode pairs disposed on mutually perpendicular lines with a maximum ratio of the calculated impedance values; and when the maximum ratio exceeds a predetermined threshold, identifying the object as a living tissue object, and allow access on the electronic device.

2. The method according to claim 1, wherein the living tissue object is a fingertip.

3. The method according to claim 2, wherein, when the maximum ratio does not exceed the predetermined threshold, the object is identified as a non-living tissue object; and if the object is identified as a non-living tissue object, denying access to the electronic device.

4. The method according to claim 3, wherein the predetermined threshold is 1.

5. The method according to claim 1, further comprising:

calculating voltage amplitude values based on the received electrical signals;

comparing the calculated voltage amplitude values for each of a pair of electrode pairs disposed on mutually perpendicular lines from the determined subset;

selecting two pairs of electrode pairs disposed on mutually perpendicular lines with a maximum difference of the voltage amplitude values; and when the maximum difference exceeds a predetermined second threshold, identifying the object as a living tissue object.

6. The method according to claim 5, wherein the predetermined second threshold is 0.

7. The method according to claim 2, further comprising:

collecting data relating to a fingerprint from electrode pairs that are in contact with the part of the object from the second set of electrode pairs to identify a user if the object is identified as a fingertip, wherein the collected data includes information relating to a papillary pattern on the fingertip.

8. The method according to claim 7, further comprising:

denying access to the electronic device when the information relating to the papillary pattern on the fingertip does not match with a pre-stored information of the papillary pattern on the fingertip for the user of the electronic device.

9. An electronic device for determining whether to allow user access based on a user input, the electronic device comprising:

a touch-sensitive area configured to detect a touch by an object, wherein a plurality of electrode pairs disposed in the a touch-sensitive area including a first set of electrode pairs and a second set of electrode pairs, and each electrode pair comprises one emitting electrode and one receiving electrode;

a generator configured to apply voltage to emitting electrodes of the second set of electrode pairs, and determine a subset of electrode pairs of the second set of electrode pairs that is in contact with a part of the object, wherein the generator is configured to apply voltage to emitting electrodes of the first set of electrode pairs, which are disposed near the determined subset of electrode pairs of the second set of electrode pairs; and a first processing circuit configured to receive electrical signals from receiving electrodes of the first set of electrode pairs, which are in a pair with emitting electrodes of the first set of electrode pairs, and calculate impedance values of respective parts of the object based on the received electrical signals, the first set of electrode pairs being electrically coupled with the first processing circuit, wherein the first processing circuit is further configured to determine a ratio of the calculated impedance values for each pair of electrode pairs disposed on mutually perpendicular lines, and if a first impedance value for one electrode pair included in electrode pairs disposed on mutually perpendicular lines is greater than a second impedance value for the other electrode pair included in the electrode pairs, the ratio of the calculated impedance values is determined as a ratio of the first impedance value to the second impedance value, and configured to select two pairs of electrode pairs disposed on mutually perpendicular lines with a maximum ratio of the calculated impedance values, when the maximum ratio exceeds a predetermined threshold, identify the object as a living tissue object, and the first processing circuit is configured to allow access on the electronic device.

10. The electronic device according to claim 9, wherein the living tissue object is a fingertip.

11. The electronic device according to claim 10, further comprising:
a second processing circuit configured to receive electrical signals comprising information on capacitance from the second set of electrode pairs, and generate information on a papillary pattern on the fingertip when the object is identified as a fingertip, wherein the second set of electrode pairs is electrically coupled with the second processing circuit.

12. The electronic device according to claim 9, wherein when the maximum ratio does not exceed the predetermined threshold, the first processing circuit is configured to identify the object as a non-living tissue object, and deny access to the electronic device when the object is identified as the non-living tissue object.

13. The electronic device according to claim 12, wherein the predetermined threshold is 1.

14. The electronic device according to claim 11, wherein the first processing circuit is further configured to calculate voltage amplitude values for each pair of electrode pairs disposed on mutually perpendicular lines based on the received electrical signals, compare the calculated voltage amplitude values, and select two pairs of electrode pairs disposed on mutually perpendicular lines with a maximum difference of voltage amplitude values, and when the maximum difference exceeds a predetermined second threshold, identify the object as the living tissue object.

15. The electronic device according to claim 14, wherein the predetermined second threshold is 0.

16. The electronic device according to claim 11, wherein the second processing circuit is further configured to collect data relating to a fingerprint from electrode pairs that are in contact with the part of the object from the second set of electrode pairs to identify a user when the object is identified as a fingertip, deny access to the electronic device when the information relating to the papillary pattern on the fingertip does not match with a pre-stored information of the papillary pattern on the fingertip for the user of the electronic device.

17. The electronic device according to claim 11, wherein the first set of electrode pairs coincides with the second set of electrode pairs, and the first processing circuit and the second processing circuit comprise an integral module.

18. The electronic device according to claim 9, the first set of electrode pairs is disposed in a frame around a touch-sensitive button on the electronic device, and the second set of electrode pairs is disposed in the touch-sensitive button.

* * * * *